United States Patent [19]

Cleare

[11] 4,173,570

[45] Nov. 6, 1979

[54] PREPARATION OF HALOGENATED ALDEHYDES

[75] Inventor: Peter J. V. Cleare, Ascot, England

[73] Assignee: Imperial Chemical Industries Limited, London, England

[21] Appl. No.: 925,627

[22] Filed: Jul. 17, 1978

Related U.S. Application Data

[62] Division of Ser. No. 862,519, Dec. 20, 1977, Pat. No. 4,128,585, which is a division of Ser. No. 737,274, Nov. 1, 1976, Pat. No. 4,085,148.

[51] Int. Cl.$^2$ .......................................... C07D 317/10
[52] U.S. Cl. ........................ 260/340.9 R; 260/340.7; 568/604
[58] Field of Search ................... 260/340.9 R, 615 A; 568/604, 340.9 R

[56] References Cited

U.S. PATENT DOCUMENTS

| | | | |
|---|---|---|---|
| 2,556,905 | 6/1951 | Copenhaver | 568/604 |
| 3,522,317 | 7/1970 | Schroeter | 568/604 |
| 3,741,986 | 6/1973 | Hartmann | 260/340.9 |

FOREIGN PATENT DOCUMENTS 6406295 1/1965 Netherlands ......................... 260/340.9

OTHER PUBLICATIONS

Le Coq, A. et al., C. R. Acad. Sc. Paris, t. 258 (Apr. 1964), Groupe 8, pp. 4085–4087.
Chem. Abstracts 79:115558m.
Chem. Abstracts 58:6867d.

*Primary Examiner*—Ethel G. Love
*Attorney, Agent, or Firm*—Cushman, Darby & Cushman

[57] ABSTRACT

The present invention relates to a process for the preparation of valuable chemical intermediates in the preparation of 2(2,2-dichlorovinyl)-3,3-dimethylcyclopropane carboxylic acid derivatives.

3 Claims, No Drawings

PREPARATION OF HALOGENATED ALDEHYDES

This is a division of application Ser. No. 862,519, filed Dec. 20, 1977, now U.S. Pat. No. 4,128,585 which is a divisional of Ser. No. 737,274, filed Nov. 1, 1976, now U.S. Pat. No. 4,085,148.

2(2,2-Dichlorovinyl)-3,3-dimethylcyclopropane carboxylic acid is an important intermediate in the production of insecticides, including for example, 3-phenoxybenzyl 2(2,2-dichlorovinyl)-3,3-dimethylcyclopropane carboxylate. The preparation of 2(2,2-dichlorovinyl)-3,3-dimethylcyclopropane carboxylic acid has been described by Farkas et al (Collection Czechoslov. Chem. Commun., (1959), 24, pp 2230–2236) by the reaction of ethyl diazoacetate with 1,1-dichloro-4-methyl-1,3-pentadiene followed by hydrolysis of the resultant ethyl ester. This process is not suitable for large scale preparation of the acid because of the difficulties of working with ethyl diazoacetate, which is a substance which can explosively decompose unless the conditions are rigorously controlled, and which is believed to be a potent carcinogen.

We have now discovered that the above acid may be prepared by a process which does not involve the use of diazoacetate.

Accordingly the present invention provides a process for the preparation of a compound of formula:

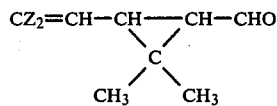

Wherein Z is chlorine or bromine, which comprises
(a) the step of reacting a compound of formula:

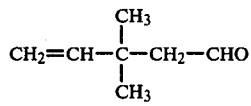

or an acetal thereof with a lower aliphatic alcohol containing up to 4 carbon atoms or an alkylene diol containing 2 or 3 carbon atoms, with a tetrahalomethane of formula $CZ_2QR$, where Z, Q and R are independently selected from chlorine and bromine provided that Q is always bromine when either of Z and R are bromine, in the presence of a free radical initiator and where an acetal is used subsequently hydrolysing the product to regenerate the free aldehyde, and
(b) the step of reacting the compound of formula:

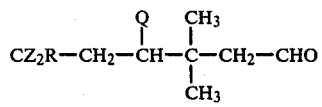

obtained in step (a) with at least two molecular equivalents of a base.

Although any tetrahalomethane of the formula $CZ_2QR$ wherein Z, Q and R are as defined above may be used, those which are particularly preferred are those which lead to compounds wherein Z is chlorine, for example carbon tetrachloride and bromotrichloromethane.

The reaction outlined in step (a) is free radical in nature and is carried out in the presence of a free-radical initiator which may be a physical initiator such as irradiation with a suitable, e.g. Ultra violet, light source, or a conventional chemical free radical catalyst such as for example benzoyl peroxide or azobisisobutyronitrile.

The reaction may conveniently be carried out using an excess of the compound of formula $CZ_2QR$ as a diluent, at temperatures in the range of 50° C. to 100° C., preferably 80°–90° C., at periods from 1 to 20 hours.

The product of the reaction of step (a) is compound of formula:

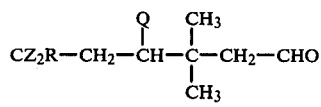

wherein Z, Q and R are as defined above. Such compounds have not been previously described and are part of the present invention. Examples of such compounds are ethyl 4-bromo-3,3-dimethyl-6,6,6-trichlorohexanal, 3,3-dimethyl-4,6,6,6-tetrabromohexanal, and 3,3-dimethyl-4,6,6,6-tetrachlorohexanal. Where the reactant in step (a) is an acetal the initial product is also an acetal, which may be converted to the aldehyde by simple hydrolysis under e.g. acid conditions. Such acetals include, for example, the dimethyl, diethyl and di-n-butyl acetals and also the acetals with ethylene glycol and propylene glycol. An acetal useful as a reactant in step (a) is 2-(2,2-dimethylbut-3-enyl)-1,3-dioxolane. Acetals produced in step (a) include 2-(3-bromo-2,2-dimethyl-5,5,5-trichloropentyl)-1,3-dioxolane and 2-(2,2-dimethyl-3,5,5,5-tetrachloropentyl)-1,3-dioxolane.

The compounds of formula:

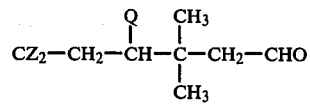

are subjected in step (b) of the process to treatment with at least two moles of a base. This part of the process involves two separate stages, cyclisation and β-elimination of hydrogen halide, but it is not clear in what order these two stages proceed, or if they proceed simultaneously. The product of the process is a cyclopropane derivative of formula:

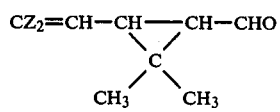

Suitable bases for carrying out the process include tertiary amines, for example pyridine, triethylamine, diethylaniline, N-methyl piperidine, and also alkali metal alkoxides, for example sodium methoxide, sodium ethoxide, and potassium t-butoxide. The step is conveniently carried out in a diluent or solvent for the reactant and the base. A particularly convenient manner of conducting this step is to heat a solution of the reactant in an alcohol corresponding to the alkali metal alkoxide being used as base for a period of from 0.5 to 20 hours.

The products of the process are as stated above compounds of formula:

$$CZ_2=CH-CH\underset{\underset{CH_3}{\diagup}\underset{CH_3}{\diagdown}}{\overset{\diagdown\diagup}{C}}CH-CHO$$

wherein Z has the meaning given herein.

They are also novel compounds and as such form part of the present invention. Examples of particular compounds of this type include 2-(2,2-dichlorovinyl)-3,3-dimethyl-1-formylcyclopropane and 2-(2,2-dibromovinyl)-3,3-dimethyl-1-formylcyclopropane.

The products of the process may be oxidised to the corresponding carboxylic acids by, for example, a metallic oxidising agent such as moist silver oxide.

The invention is illustrated by the following Examples.

EXAMPLE 1

This example illustrates the preparation of 4-bromo-3,3-dimethyl-6,6,6-trichlorohexanal.

A stirred mixture of bromotrichloromethane (7.9 g) and 3,3-dimethylpent-4-en-1-al (1.12 g) was irradiated under a nitrogen atmosphere for 1 hour using a 500 watt mercury vapour lamp during which time the mixture temperature rose from the ambient temperature to 60° C. After this period the excess bromotrichloromethane was removed by evaporation under reduced pressure and the residual oil shown by mass spectroscopy to contain about 10% of the desired product, the remainder being unreacted starting material.

EXAMPLE 2

This example illustrates the preparation of 2-(2,2-dimethyl-but-3-enyl)-1,3-dioxolane, of formula:

$$CH_2=CH-\underset{\underset{CH_3}{|}}{\overset{\overset{CH_3}{|}}{C}}-CH_2-CH\underset{O-CH_2}{\overset{O-CH_2}{\diagup\diagdown|}}$$

A stirred mixture of 3,3-dimethylpent-4-en-1-al (22.4 g), ethylene glycol (12.4 g), toluene (100 ml), and p-toluene sulphonic acid (0.25 g) was refluxed for 3.75 hours in an apparatus fitted with a Dean and Starke water separator. About half the toluene was then removed by distillation at atmospheric pressure and the residual mixture washed with saturated sodium bicarbonate solution (3×50 ml), and dried over anhydrous magnesium sulphate. After removal of the remaining solvent by evaporation under reduced pressure the residual oil was distilled to yield 2-(2,2-dimethylbut-3-enyl)-1,3-dioxolane, pale yellow oil, b.p. 69°-72° C./14-15 mm.

EXAMPLE 3

This example illustrates the preparation of 2-(3-bromo-2,2-dimethyl-5,5,5-trichloropentyl)-1,3-dioxolane, of formula:

$$CCl_3-CH_2-CHBr-\underset{\underset{CH_3}{|}}{\overset{\overset{CH_3}{|}}{C}}-CH_2-CH\underset{O-CH_2}{\overset{O-CH_2}{\diagup\diagdown|}}$$

A stirred mixture of 2-(2,2-dimethylbut-3-enyl)-1,3-dioxide 15.6 g) and bromotrichloromethane (79.4 g) was irradiated under a nitrogen atmosphere for 12 hours using a 500 watt mercury vapour lamp ($\lambda=257$ nm). The excess bromotrichloromethane was removed by evaporation under reduced pressure keeping the mixture temperature below 40° C. The residual oil was distilled carefully to yield substantially pure 2-(3-bromo-2,2-dimethyl-5,5,5-trichloropentyl)-1,3-dioxolane (b.p. 76°-80° C./0.04 mm).

EXAMPLE 4

This example illustrates the preparation of 4-bromo-3,3-dimethyl-6,6,6-trichlorohexanal.

Sulphuric acid (5% w/v aqueous solution, 20 ml) was added dropwise over a period of 5 minutes to a stirred mixture of 2-(3-bromo-2,2-dimethyl-5,5,5-trichloropentyl)-1,3-dioxolane (3.54 g) and 1,4-dioxane (2.0 ml), at the ambient temperature. The resultant mixture was heated at 100° C. for 1.5 hours, cooled to the ambient temperature and shaken with chloroform (10 ml). The chloroform layer was separated, washed with saturated sodium bicarbonate solution (3×100 ml) and with water, and dried over anhydrous magnesium sulphate. Removal of the solvent by evaporation under reduced pressure yielded a pale yellow oil consisting essentially of 4-bromo-3,3-dimethyl-6,6,6-trichlorohexanal.

EXAMPLE 5

This example illustrates the preparation of 2,2-dimethyl-3-(2,2-dichlorovinyl)-1-formylcyclopropane, of formula:

$$CCl_2=CH-CH\underset{\underset{CH_3}{\diagup}\underset{CH_3}{\diagdown}}{\overset{\diagdown\diagup}{C}}CH-CHO$$

4-Bromo-3,3-dimethyl-6,6,6-trichlorohexanal (0.93 g) is dissolved in ethyl alcohol (10 ml) and added dropwise to a solution of sodium (0.15 g) in ethyl alcohol (2.0 ml) at the ambient temperature over 5 minutes. The mixture is stirred at the ambient temperature for 15 minutes and at 40° C. for 15 minutes, after which it is cooled, and the solvent evaporated under reduced pressure. The residue is partitioned between water (10 ml) and chloroform (10 ml) and the chloroform phase washed with water (5 ml) and dried over anhydrous magnesium sulphate. After removal of the solvent by evaporation under reduced pressure the residual oil may be shown by mass spectroscopy to consist principally of 2,2-dimethyl-3-(2,2-dichlorovinyl)-1-formylcyclopropane.

EXAMPLE 6

By similar procedures to those set out in the preceeding Examples 2,2-dimethyl-3(2,2-dibromovinyl)-1-formylcyclopropane may be prepared from 3,3-dimethylpent-4-en-1-al and carbon tetrabromide.

EXAMPLE 7

Using a procedure similar to that outlined in Example 3 but without the use of irradiation, 2-(2,2-dimethyl-3,5,5,5-tetrachloropentyl) 1,3-dioxolane may be obtained from 2-(2,2-dimethylbut-3-enyl)-1,3-dioxolane and carbon tetrachloride, using benzoyl peroxide as a free radical catalyst.

I claim:

1. An acetal of a compound of formula:

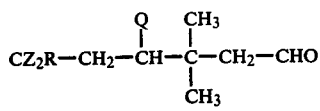
with a lower aliphatic alcohol containing up to 4 carbon atoms or an alkylene diol containing 2 or 3 carbon atoms, where Q, R and Z are independently selected from chlorine or bromine provided that Q is always bromine when either of R and Z are bromine.
2. 2-(3-Bromo-2,2-dimethyl-5,5,5-trichloropentyl)-1,3-dioxolane.
3. 2-(2,2-Dimethyl-3,5,5,5-tetrachloropentyl)-1,3-dioxolane.
* * * * *